(12) United States Patent
Wolf et al.

(10) Patent No.: US 6,304,021 B1
(45) Date of Patent: Oct. 16, 2001

(54) METHOD AND APPARATUS FOR OPERATING A MICROACOUSTIC SENSOR ARRAY

(75) Inventors: Konrad Wolf, Walzbachtal; Hans Hecht, Korntal-Muenchingen; Falk Herrmann, Eningen, all of (DE)

(73) Assignee: Robert Bosch GmbH, Stuttgart (DE)

(*) Notice: Subject to any disclaimer, the term of this patent is extended or adjusted under 35 U.S.C. 154(b) by 0 days.

(21) Appl. No.: 09/581,111
(22) PCT Filed: Sep. 22, 1999
(86) PCT No.: PCT/DE99/03024
§ 371 Date: Jun. 8, 2000
§ 102(e) Date: Jun. 8, 2000
(87) PCT Pub. No.: WO00/26659
PCT Pub. Date: May 11, 2000

(30) Foreign Application Priority Data

Nov. 4, 1998 (DE) ............................................... 198 50 801

(51) Int. Cl.[7] .............................. G01N 29/02; G01L 41/08
(52) U.S. Cl. ........................................................... 310/313 B
(58) Field of Search ............................. 310/313 R, 313 B

(56) References Cited

U.S. PATENT DOCUMENTS

| 4,281,350 | * | 7/1981 | Maerfeld et al. | ................ 310/313 B |
| 5,051,645 | | 9/1991 | Brace | ............................. 310/313 D |
| 5,850,118 | * | 12/1998 | Toda | ................................ 310/313 R |

FOREIGN PATENT DOCUMENTS 87 02134 A    4/1987  (WO) ............................. G01N/29/00

* cited by examiner

*Primary Examiner*—Thomas M. Dougherty
(74) *Attorney, Agent, or Firm*—Michael J. Striker

(57) ABSTRACT

A method and apparatus are proposed for operating a microacoustic sensor arrangement, for example, to determine the physical characteristics of a measurement medium. Acoustic surface waves with predetermined wave modes are generated and detected by electroacoustic transducers (6) and a measurement for the physical characteristics of the measurement medium is determined from their propagation behavior along a propagation path. In addition, a sagittally polarized surface wave is generated in the area of the surface of the substrate (5; 22) on which the measurement medium is located.

10 Claims, 3 Drawing Sheets

METHOD AND APPARATUS FOR OPERATING A MICROACOUSTIC SENSOR ARRAY

PRIOR ART

The invention is directed to a method and apparatus for operating a microacoustic sensor arrangement, in particular for eliminating impurities in the sensor arrangement, according to the preamble of the main claim.

Microacoustic sensor arrangements are used with so-called acoustic SAW or surface wave components (SAW=Surface Acoustic Wave) as sensors for a wide range of physical quantities, especially in liquids. In this connection, an important field is that of the measurement of electrical quantities such as the dielectric constant and/or conductivity, the measurement of mechanical quantities such as density and/or viscosity and the examination of chemical properties, e.g., the presence of specific substances in liquids.

A known sensor arrangement is based on a measurement principle described, for example, in the article "A Study of Love-wave Acoustic Sensors", J. Du, G. L. Hardling, P. R. Ogilvy and M. Lake, in the technical journal Sensors and Actuators A56 (1996), pages 211 to 219. In the measurement construction described in this article, a sensor is realized which operates with horizontally polarized acoustic shear waves, so-called leaky waves or surface skimming bulk waves (SSB waves) or Love waves. These acoustic wave modes are generated and also detected by interdigital transducers, as they are called, which are also known per se from the above-mentioned prior art, so that the desired sensor signal can be obtained from the propagation behavior on a propagation or measurement path.

Depending on the required measurement construction, different materials and arrangements are used for the sensor elements, e.g., a determined substrate material for the sensor elements, a given wave propagation direction, possibly also a specific layer construction on the substrate material and a determined arrangement of the sensor elements formed as electroacoustic transducers. In this connection, one or more of the above-mentioned acoustic wave modes, known per se, occur; these acoustic wave modes differ from one another with respect to possible measurement sensitivity, propagation speed, an acoustoelectric coupling factor and susceptibility to transverse effects, etc. and therefore determine the suitability of a specific sensor type for a specific measurement task.

As was mentioned, the acoustic wave modes described above and known from the prior art have to do with horizontally polarized acoustic shear waves in which a wave propagating along the surface of the substrate on which the electroacoustic transducer is located is utilized.

Aside from measurement sensitivity, other boundary conditions such as contamination, aggressive media in a liquid and cross-sensitivities must be taken into account when using SAW components as sensors, especially for examining liquids. When used in liquid media such as those applied in the automotive field (e.g., oils, fuels, combustion liquid, etc.) or in biological sensor equipment, susceptibility to contamination plays a central role because a depositing of particles on the surface of the sensor leads directly to corruption of the measurement signal due to the increased mass. Therefore, as regards practical use of these sensors, where regular exchange of the sensor element can often not be tolerated, the risk that components of the measurement fluid will be deposited on the surface of the sensor or substrate constitutes an important problem.

ADVANTAGES OF THE INVENTION

The above-mentioned method for operating a microacoustic sensor arrangement, in particular for eliminating contamination in the sensor arrangement, and an apparatus for carrying out the method are advantageously further developed according to the invention by the characterizing features of the main claim and apparatus claim. According to the invention, a method is advantageously provided by which a cleaning of sensor arrangements of the generic type can be achieved during operation without external auxiliary means.

The invention makes use of the characteristic that, aside from the shear modes, other acoustic wave modes with predominantly sagittal polarization (for example, Rayleigh modes, as they are called) occur in many substrate materials for the electroacoustic transducers, e.g., in certain quartz sections, lithium tantalate sections and lithium niobate sections which can be used for the above-described SAW sensors with acoustic shear modes.

Because of the particle movement in these wave modes which extend vertical to the substrate surface, pressure waves are directly radiated in a liquid layer located on the surface so that, although it is impossible to use these wave modes for purposes of sensors, they can be utilized for cleaning purposes on the surface of the substrate. The radiation of ultrasonic waves of this type in a liquid causes transport phenomena, known per se, in the liquid, which transport phenomena can be used for accelerated dissolution of particles deposited on the surface of the substrate.

Apart from cleaning the sensor surface, desorption processes of molecules adsorbed on the sensor surface can also be reinforced by the utilized sound waves, which can be made use of especially in chemical sensors which are mostly based on a reversible adsorption of chemical substances.

These acoustic wave modes with sagittal polarization frequently occur in a propagation direction that is rotated by 90° in relation to the above-mentioned shear modes for the sensors, so that particularly simple arrangements are possible.

For this purpose, it is possible to make use of the effect that an increase in the frequency of the ultrasonic wave generated with the sagittal wave modes generally has a positive effect on the material removal and cleaning processes. In the microsensors used according to the invention with the interdigital transducers, which are known per se from the prior art mentioned above and are used as electroacoustic transducers, ultrasonic frequencies of several-times ten to several hundred megahertz can be realized in a simple manner. Since these transducers can be arranged directly on the surface of the substrate to be cleaned, this surface having a typical size of a few $mm^2$, the outputs required for achieving an extensive cleaning effect are relatively low.

A determined embodiment form of the sensor arrangement with SH-APM sensors (SH-APM=Shear Horizontal Acoustic Plate Modes) makes use of the horizontally polarized plate shear modes in the thin plates of suitable piezoelectric materials, which plate shear modes are capable of propagation. These wave modes can be excited by the metallic interdigital transducers arranged on the plate surfaces. These wave modes are accordingly shear waves that are reflected repeatedly between the two plate surfaces. When one or both surfaces are wetted with a measurement liquid, a viscous coupling is brought about, so that the wave damping and the propagation speed depend on the density-viscosity product of the measuring liquid.

Further, these sensor arrangements with the SH-APM sensors are suitable as gravimetric chemical or biological sensors and, when the acoustoelectrical effect is utilized, for examining conductive liquids. As a rule, the measurement medium is applied to the surface of the substrate remote of the sensor transducers for this purpose, since the sensitive sensor transducers are protected in this way. The cleaning transducers can accordingly be arranged on the wetted side of the substrate in this embodiment form.

To summarize, all of the embodiment forms result in advantageous sensor arrangements which allow a simple and advantageous cleaning process for the measurement-sensitive areas of the sensor arrangement. To achieve a cleaning effect at the sensor surface, an integration of cleaning transducers for exciting sagittally polarized acoustic surface waves can advantageously be carried out in connection with arrangements of the sensor transducers for generating horizontally polarized acoustic shear modes for measuring purposes. The arrangement of the cleaning transducers is carried out in sensor arrangements, e.g., with the first mode types comprising Love modes, leaky waves or SSB waves, on the same substrate surface as the sensor transducer or, with the second mode types comprising the SH-APM sensors, on the substrate surface located opposite the sensor transducers.

An arrangement of one or more cleaning transducers next to the sensor transducer or inside the sensor element, possibly with a protective layer of adhesion-reducing material above the sensor element and cleaning transducer, can be produced in a simple manner. The cleaning of the sensor surface and an acceleration of desorption processes of adsorbed molecules in the sensor arrangement can be carried out without external mechanical action and during operation. This results in an increase in the duration of use and in long-term stability as well as expanded possibilities for use.

No other process steps are necessary during production for generating the cleaning transducer required for this purpose because they can be produced with the sensor transducers in one process step. The cleaning transducers act directly on the sensor surface and there is only a slight increase, if any, in space requirements compared with conventional sensor arrangements.

These and other features of preferred further developments of the invention are contained in the claims, including the dependent subclaims, as well as in the description and drawings, and the individual features are realized individually or collectively in the form of sub-combinations in the embodiment form of the invention and in other fields and can show advantageous constructions which are also capable of protection in themselves and for which protection is claimed herein:

DRAWING

An embodiment example of a sensor arrangement for carrying out the method according to the invention is described with reference to the drawing.

Figure 2:
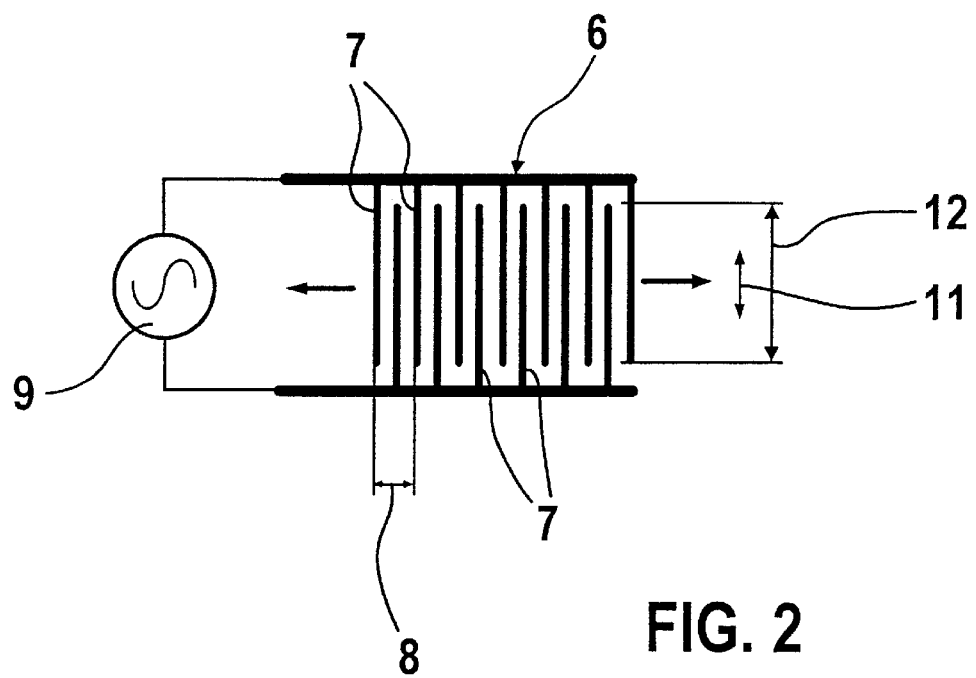
FIG. 2 shows a detailed view of an interdigital transducer for generating and detecting acoustic wave modes.
Figure 3:
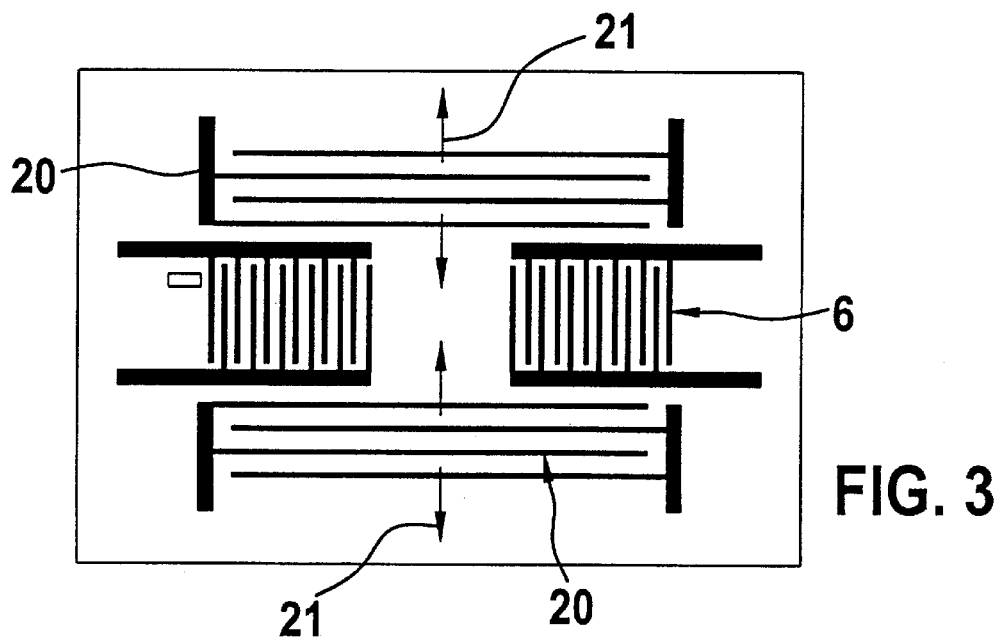
Figure 4:
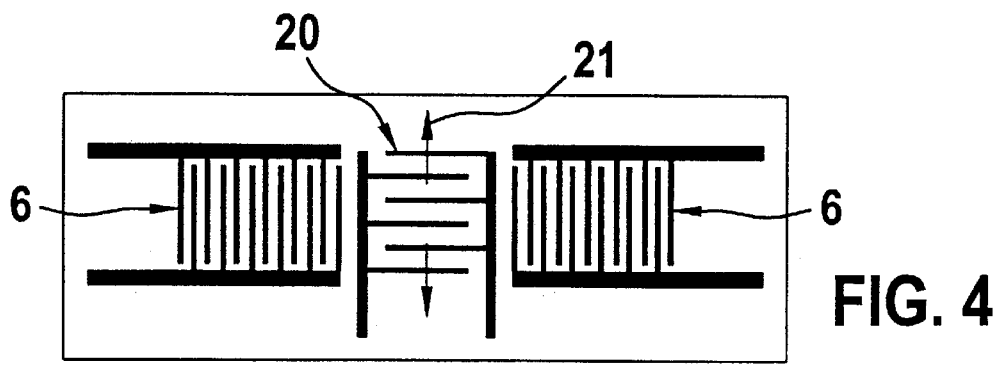
Figure 5:
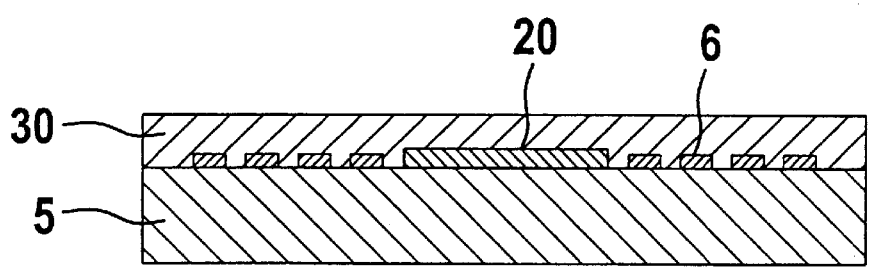
Figure 6:
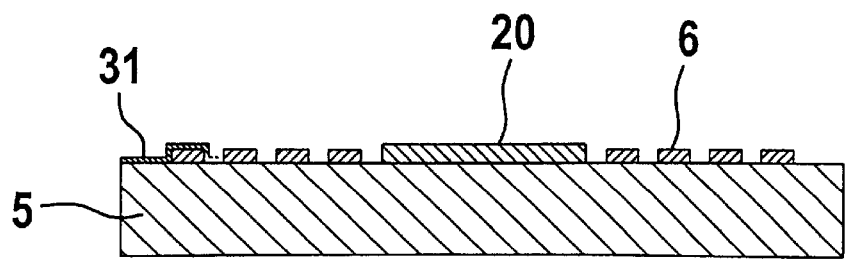
Figure 7:
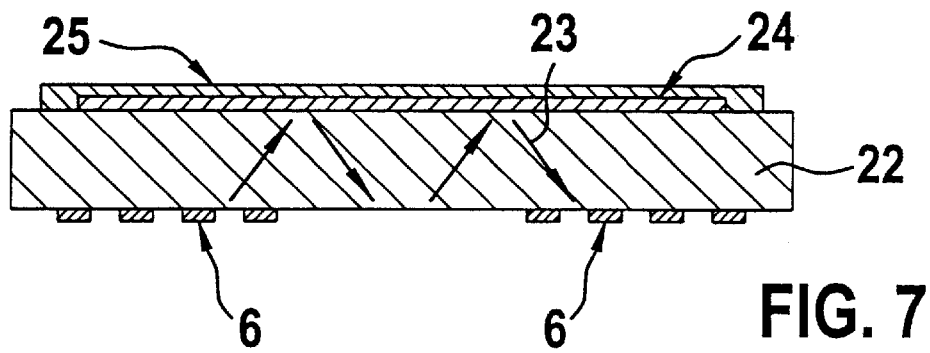
Figure 8:
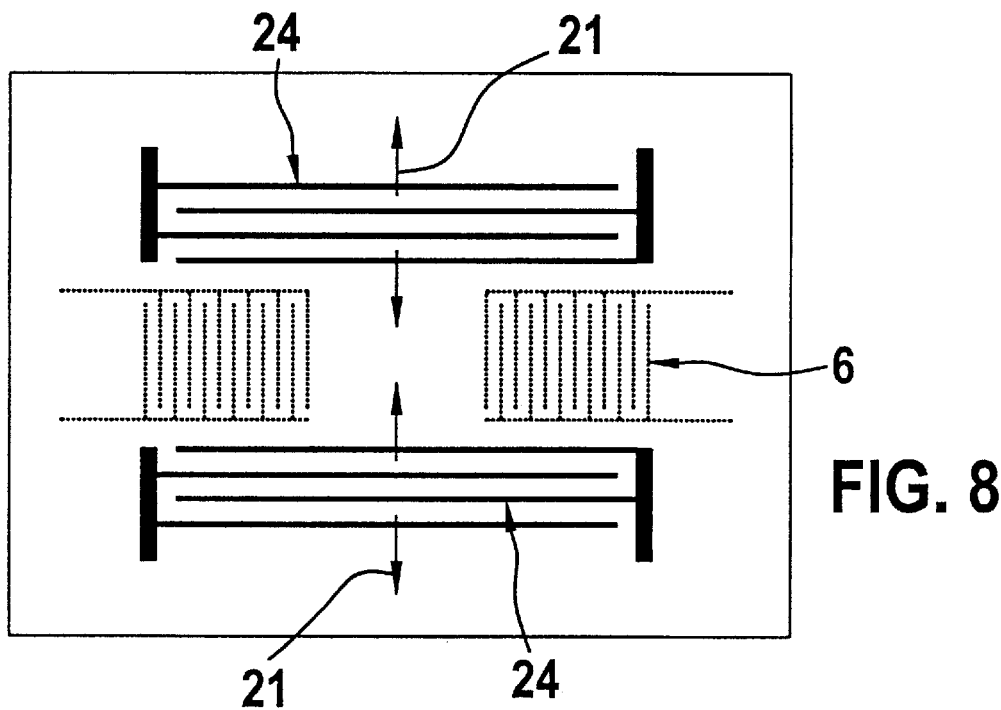
Figure 9:
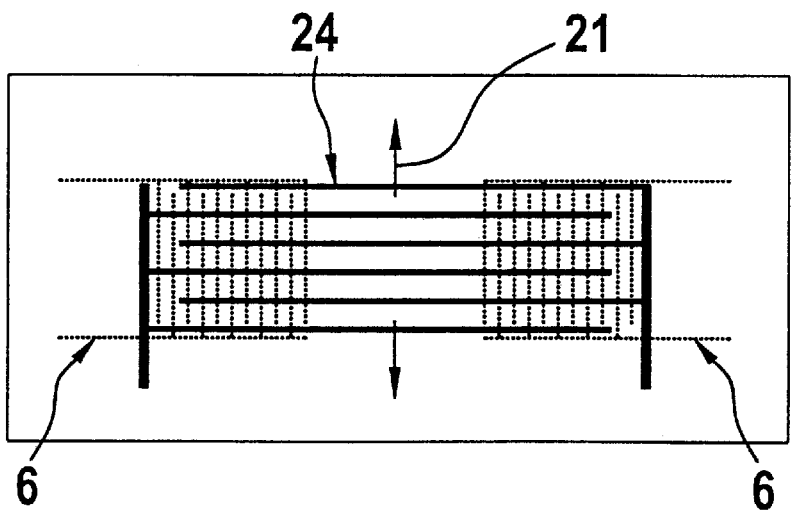

FIGS. 3 and 4 each show an arrangement of interdigital transducers according to FIG. 2 as cleaning transducers for generating sagittally polarized acoustic wave modes of the first mode types;

FIGS. 5 and 6 show sections of the embodiment form according to FIG. 4 with a waveguide layer for the Love mode types according to FIG. 5 and a protective layer for the leaky or SSBW mode types according to FIG. 6;

FIG. 7 shows a section through another embodiment example of a sensor arrangement for the second mode types in which a repeatedly reflected shear wave is used as measurement signal;

FIG. 8 shows a first example of an arrangement of cleaning transducers according to FIG. 7; and FIG. 9 shows a second example of an arrangement of cleaning transducers according to FIG. 7.

DESCRIPTION OF THE EMBODIMENT EXAMPLES

Figure 1:
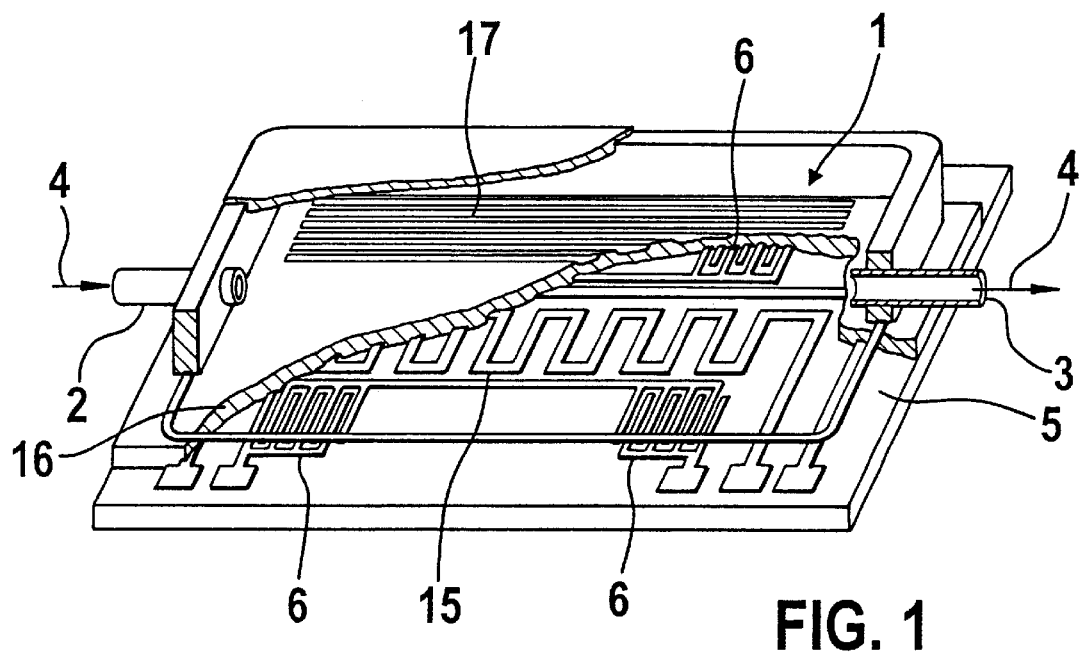
FIG. 1 shows, by way of example, a schematic view of a sensor arrangement for determining the density and the viscosity of a liquid flowing through the sensor arrangement.

FIG. 1 is a sectional schematic view showing a sensor arrangement 1 through which a measurement liquid flows from an input 2 to an output 3 in the direction of arrow 4 for determining its density and viscosity. The principal component of the proposed sensor arrangement 1 is a substrate 5 which is polished on one side and formed of a piezoelectric material in which horizontally polarized acoustic shear modes of sensor base elements can be excited and are capable of propagation. Suitable substrate materials are Y-rotated quartz sections, some lithium niobate sections and lithium tantalate sections as well as appropriately polarized piezoelectric ceramics.

An arrangement of metallic interdigital transducers (IDTs) 6 which are described more fully with reference to FIG. 2 are located on the polished surface of the substrate 5. These interdigital transducers 6 are made of aluminum, titanium, chromium, gold or platinum, for example, possibly on an adhesive layer of silicon, and are used for excitation and detection of the acoustic surface waves.

Further, in the embodiment example according to FIG. 1, a meander-shaped thin-film temperature resistor 15 is arranged next to or between the base elements with the IDT 6 on the surface of the substrate 5, since the viscosity in particular is highly dependent on temperature and temperature is therefore another important measurement quantity. The same material as that used for the IDT 6 can also advantageously be used as the material for the thin-film temperature resistor 15, namely, titanium/platinum or titanium/platinum/titanium, wherein the adhesive layer can be either titanium or silicon.

FIG. 2 shows one of the interdigital transducers 6 in detail, wherein transducer fingers 7 can generate acoustic waves with wavelength 8 (center frequency) by excitation through an electric voltage at an input 9. This results in an acoustic surface wave, i.e., especially a shear wave in the polarization direction indicated by arrow 11, with the aperture according to arrow 12. According to an embodiment example, not shown here, the transducer fingers 7 can also be split up within the cycles or periods into two individual fingers or also split fingers, so that $\lambda/8$ fingers are formed. In this case, there is a factor of 2 between the electrical and mechanical periods, so that an elimination or at least a reduction of internal reflections and of the so-called triple-transit echo (TTE) can be achieved.

FIG. 3 is a schematic view showing an arrangement of interdigital transducers 6 as sensor transducers which are arranged on the substrate 5 in such a way that the above-described horizontally polarized shear waves propagating along the surface are utilized for measurement. In this case, there are other interdigital transducers 20 which are rotated by 90° or by another angle corresponding to the propagation direction of the utilized wave modes and which are used for exciting sagittally polarized wave modes in the propagation direction according to arrow 21 and accordingly act as cleaning transducers. These cleaning transducers 20 are located in the same masking planes of the substrate 5 as the interdigital transducers 6 acting as sensor transducers.

Therefore, in accordance with FIG. 3, two cleaning transducers 20 extending over the entire length of the sensor can be arranged on both sides of the sensor transducers 6. The sagittally polarized acoustic wave modes excited by the transducers 20 propagate along the surface in the direction indicated by arrow 21 and, in so doing, radiate ultrasonic energy in the liquid located above it. The ratio between the transducer periods of the cleaning transducers 20 and the spacing between the two cleaning transducers 20 must be selected in such a way that sufficient energy for a cleaning effect is available over the entire sensor surface.

A special advantage of the arrangement according to FIG. 3 is that no cleaning transducers 20 are located in the area of the active sensor surface with the sensor transducers 6 and their propagation paths. The resulting sensor element with the cleaning transducers 20 can therefore be constructed as a delay line, as shown in FIG. 3, or as a resonator (not shown here). Alternatively, the two cleaning transducers 20 can also be divided into a plurality of smaller transducers, also not shown, for improved impedance matching.

In a second embodiment form shown in FIG. 4, one or more cleaning transducers 20 are arranged vertically between the sensor transducers 6 directly on the delay path. An advantage of this arrangement consists in the more direct action of the ultrasonic waves on the surface to be cleaned and the reduced space requirement in comparison to the arrangement according to FIG. 3. In both embodiment forms according to FIG. 3 and FIG. 4, an acoustically thin adhesion-reducing layer, not shown, e.g., Teflon or other chemically inert materials for protecting the IDT 6, can be provided above the transducers 6 and 20 to reinforce the cleaning action.

FIG. 5 shows a section through the arrangement according to FIG. 4 in which a waveguide layer 30 is arranged over the transducers 6 and 20 for application of Love mode waves. A section according to FIG. 6 shows an embodiment form for use with leaky waves or SSBW waves in which a thin protective film 31 can again be placed over the transducers 6 and 20.

FIG. 7 shows an embodiment example of a sensor arrangement with the SH-APM sensors in which a shear wave which is reflected repeatedly inside between the two surfaces of a substrate 22 (see arrow 23) is utilized for the sensor transducer 6. In this case, in contrast to the embodiment example according to FIG. 1, the sensor transducer 6 is located on the surface of the substrate 22 facing away from the measurement medium. In order to achieve a cleaning effect on the measurement surface of the substrate 22 in this case, one or more cleaning transducers 24 for exciting wave modes with sagittal polarization is/are arranged next to the measurement path in the measurement medium according to FIG. 8 and on the measurement path in the measurement medium according to FIG. 9. The cleaning transducers 24 can also be divided into a plurality of smaller transducers in this case, e.g., for reasons pertaining to impedance. Further, it is also possible in this case to provide an adhesion-reducing layer 25 or a protective layer above the cleaning transducer 24 according to FIG. 7.

What is claimed is:

1. Method for operating a microacoustic sensor arrangement in which acoustic surface waves with predetermined wave modes are generated and detected by electroacoustic transducers (6) in sensor base elements and a measurement for the physical characteristics of a measurement medium is determined from their propagation behavior along a propagation path, characterized in that a sagittally polarized surface wave is generated in the area of the surface of the sensor base element on which the measurement medium is located.

2. Method according to claim 1, characterized in that the sagittally polarized surface wave for cleaning the surface wetted with the measurement medium is utilized in a special cleaning process.

3. Method according to claim 1, characterized in that the sagittally polarized surface wave for cleaning the surface wetted with the measurement medium is utilized during the operation of the sensor arrangement.

4. Apparatus for carrying out the method according to claim 1, characterized in that the electroacoustic transducers are formed by interdigital transducers (6) arranged on a substrate (5) and their transducer fingers (7) are constructed in such a way that the required wave modes can be generated with a suitable oscillator frequency, and in that there are sensor transducers (6) as electroacoustic transducers for measurement and there are cleaning transducers (20; 24) in or at the propagation path of the sensor transducers (6), wherein the sagittally polarized wave modes of the cleaning transducers (20; 24) propagate so as to be rotated at an angle of 90°, or at another angle corresponding to the propagation direction of the wave modes, relative to the first propagation path.

5. Apparatus according to claim 4, characterized in that the cleaning transducers (20) are arranged on both sides of the propagation path extending between the sensor transducers (6).

6. Apparatus according to claim 4, characterized in that one or more cleaning transducers (20) are arranged in the propagation path acting as delay path between the sensor transducers (6).

7. Apparatus according to claim 4, characterized in that the substrate (22) is formed as a component part of a SH-APM sensor, wherein the sensor transducers (6) are arranged on the surface of the substrate (22) remote of the measurement medium and the cleaning transducers (24) are arranged on the oppositely located surface of the substrate (22) which is wetted by the measurement medium.

8. Apparatus according to claim 7, characterized in that at least the cleaning transducers (20; 24) are provided with an adhesion-reducing layer (25) for the measurement medium.

9. Apparatus according to claim 4, characterized in that the cleaning transducers (20; 24) are divided into a quantity of smaller transducers for impedance matching.

10. Apparatus according to claim 1, characterized in that at least one temperature sensor made from the same material as the sensor transducers (6) and cleaning transducers (20; 24) is arranged on the substrate (5; 22) on the side facing the measurement medium.

* * * * *